(12) United States Patent
Iwamoto et al.

(10) Patent No.: US 10,618,050 B2
(45) Date of Patent: Apr. 14, 2020

(54) MICROFLUIDIC DEVICE FOR REDUCING FLUCTUATION IN THE SOLUTION FEEDING RATE OF A REACTION SOLUTION

(71) Applicant: Panasonic Intellectual Property Management Co., Ltd., Osaka (JP)

(72) Inventors: Narimasa Iwamoto, Mie (JP); Takao Miyai, Osaka (JP); Nobuyuki Miyagawa, Osaka (JP); Tsutomu Ichihara, Osaka (JP); Masashi Ishimaru, Osaka (JP); Toshihiko Sato, Osaka (JP); Hiroaki Tachibana, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 116 days.

(21) Appl. No.: 15/504,552

(22) PCT Filed: Feb. 26, 2016

(86) PCT No.: PCT/JP2016/001034
§ 371 (c)(1),
(2) Date: Feb. 16, 2017

(87) PCT Pub. No.: WO2016/143283
PCT Pub. Date: Sep. 15, 2016

(65) Prior Publication Data
US 2018/0056298 A1 Mar. 1, 2018

(30) Foreign Application Priority Data
Mar. 9, 2015 (JP) .................................. 2015-046337

(51) Int. Cl.
*B01L 7/00* (2006.01)
*G01N 37/00* (2006.01)
(Continued)

(52) U.S. Cl.
CPC .............. *B01L 7/525* (2013.01); *B01J 19/00* (2013.01); *B01J 19/0053* (2013.01);
(Continued)

(58) Field of Classification Search
None
See application file for complete search history.

(56) References Cited

U.S. PATENT DOCUMENTS

| 6,440,645 | B1 | 8/2002 | Yon-Hin et al. |
| 6,677,114 | B1 | 1/2004 | Schneider et al. |

(Continued)

FOREIGN PATENT DOCUMENTS

| JP | 2002-018271 A | 1/2002 |
| JP | 2002-058470 A | 2/2002 |

(Continued)

OTHER PUBLICATIONS

J. Xiaoyu et al., "Polydimethylsiloxane (PDMS)-based spiral channel PCR Chip", Electronics Letters, vol. 41, No. 16, Aug. 4, 2005, pp. 890-891.

(Continued)

*Primary Examiner* — Christopher Adam Hixson
*Assistant Examiner* — Michelle Adams
(74) *Attorney, Agent, or Firm* — McDermott Will & Emery LLP

(57) ABSTRACT

A microfluidic device includes a flow path through which a reaction solution flows, and an introducing portion for introducing the reaction solution into the flow path, wherein the flow path passes alternately and repeatedly several times through a first temperature region and a second temperature region having different predetermined temperatures, and the flow path includes the repeating unit portions passing through the first temperature region and the second temperature region, the repeating unit portions having decreasing lengths as the repeating unit portions are located farther away from the introducing portion.

4 Claims, 9 Drawing Sheets

(51) Int. Cl.
*B01J 19/00* (2006.01)
*C12M 1/00* (2006.01)
*B81B 1/00* (2006.01)
*C12M 1/34* (2006.01)
*B01L 3/00* (2006.01)
*C12M 1/12* (2006.01)
*C12M 3/06* (2006.01)
*C12N 15/10* (2006.01)

(52) U.S. Cl.
CPC .............. *B01L 3/5027* (2013.01); *B81B 1/00* (2013.01); *C12M 1/00* (2013.01); *C12M 1/34* (2013.01); *C12M 23/04* (2013.01); *C12M 23/16* (2013.01); *G01N 37/00* (2013.01); *B01L 2300/0816* (2013.01); *B01L 2300/0883* (2013.01); *B01L 2300/1805* (2013.01); *B01L 2400/0406* (2013.01); *B01L 2400/0487* (2013.01); *C12N 15/102* (2013.01)

(56) References Cited

U.S. PATENT DOCUMENTS

| | | | |
|---|---|---|---|
| 6,764,817 | B1 | 7/2004 | Schneider |
| 8,277,759 | B2* | 10/2012 | Sundberg ............ B01L 3/50273 216/52 |
| 9,849,436 | B2* | 12/2017 | Tachibana ......... B01L 3/502746 |
| 2002/0097632 | A1 | 7/2002 | Kellogg et al. |
| 2002/0106786 | A1 | 8/2002 | Carvalho et al. |
| 2003/0106797 | A1 | 6/2003 | Schneider et al. |
| 2003/0152491 | A1 | 8/2003 | Kellogg et al. |
| 2004/0091943 | A1 | 5/2004 | Schneider |
| 2004/0262160 | A1 | 12/2004 | Schneider et al. |
| 2005/0089930 | A1 | 4/2005 | Schneider et al. |
| 2005/0153346 | A1 | 7/2005 | Schneider |
| 2005/0158847 | A1* | 7/2005 | Fosdick .............. B01L 3/50273 435/287.2 |
| 2006/0160097 | A1 | 7/2006 | Nakatani et al. |
| 2009/0010915 | A1 | 1/2009 | Schneider |
| 2009/0162929 | A1* | 6/2009 | Ikeda ...................... B01L 7/525 435/303.1 |
| 2009/0311713 | A1* | 12/2009 | Pollack ............. B01L 3/502792 435/287.2 |
| 2010/0304446 | A1 | 12/2010 | Davies et al. |
| 2011/0086361 | A1* | 4/2011 | Klunder ............... C12Q 1/6834 435/6.12 |
| 2011/0212516 | A1* | 9/2011 | Ness ..................... B01F 3/0807 435/303.1 |
| 2012/0328488 | A1 | 12/2012 | Puntambekar et al. |
| 2014/0220668 | A1 | 8/2014 | Tachibana et al. |
| 2015/0238963 | A1 | 8/2015 | Han et al. |
| 2016/0199840 | A1 | 7/2016 | Tachibana et al. |

FOREIGN PATENT DOCUMENTS

| | | |
|---|---|---|
| JP | 2003-529044 A | 9/2003 |
| JP | 2004-061320 A | 2/2004 |
| JP | 2012-533757 A | 12/2012 |
| JP | 2013-061354 A | 4/2013 |
| WO | 2013/027393 A1 | 2/2013 |
| WO | 2015/019626 A1 | 2/2015 |

OTHER PUBLICATIONS

M. Hashimoto et al., "Rapid PCR in continuous flow device", Lab Chip, royal society of Chemistry, vol. 4, No. 6, Jan. 1, 2004, pp. 638-645.

Extended European Search Report issued in Application No. 16761261.3 dated Mar. 9, 2018.

International Search Report issued in Application No. PCT/JP2016/001034 dated May 31, 2015, with English translation.

* cited by examiner

MICROFLUIDIC DEVICE FOR REDUCING FLUCTUATION IN THE SOLUTION FEEDING RATE OF A REACTION SOLUTION

RELATED APPLICATIONS

This application is the U.S. National Phase under 35 U.S.C. § 371 of International Application No. PCT/JP2016/001034, filed on Feb. 26, 2016, which in turn claims the benefit of Japanese Application No. 2015-046337, filed on Mar. 9, 2015, the disclosures of which are incorporated by reference herein.

TECHNICAL FIELD

The present disclosure relates to microfluidic devices.

BACKGROUND ART

Microfluidic devices have flow paths through which reaction solutions flow, and can react the reaction solutions containing an extremely small amount of sample or reagent. Examples of such microfluidic devices include microreaction devices (microreactors), integrated DNA devices, or microelectrophoretic devices.

For example, microfluidic devices are used in reaction devices which cause desired changes in temperature of the reaction solutions flowing through the flow paths. Use of the microfluidic devices can change the temperature of the reaction solutions at high speed.

Nucleic acid amplification devices have been known which amplify target nucleic acids through repeating change in temperature of the reaction solution. Microfluidic devices used as such nucleic acid amplification devices can amplify target nucleic acids at high speed.

For example, Patent Literature 1 discloses a device including a plurality of divided sections having different temperatures, and a serpentine flow path such that a reaction solution repeatedly passes through the sections having different temperatures.

Such a configuration can bring a desired change in temperature to the reaction solution only through traveling of the reaction solution through the serpentine flow path, achieving high-speed amplification of nucleic acid by using a reaction solution containing the nucleic acid.

CITATION LIST

Patent Literature

PTL 1: Japanese Unexamined Patent Application Publication No. 2002-18271

SUMMARY OF THE INVENTION

Technical Problems

Unfortunately, this device has an uneven solution feeding rate of the reaction solution flowing through the flow path. Specifically, the solution feeding rate of the reaction solution in a region near the start point of the flow path is different from that in a region near the end point thereof. The difference in the solution feeding rate fluctuates the reaction time of the reaction solution in the reaction portion.

The present disclosure has been made to solve these problems. An object of the present disclosure is to provide a microfluidic device which can perform a reaction of a reaction solution flowing through a flow path in a reaction time close to a predetermined reaction time.

Solution to Problem

To achieve this object, one aspect of according to the present disclosure microfluidic device is a microfluidic device including: a flow path through which a reaction solution flows; and an introducing portion for introducing the reaction solution into the flow path, wherein the flow path passes alternately and repeatedly several times through a first temperature region and a second temperature region having different predetermined temperatures, and the flow path includes repeating unit portions passing through the first temperature region and the second temperature region, the repeating unit portions having decreasing lengths along a solution feeding direction of the reaction solution as the repeating unit portions are located farther away from the introducing portion.

Advantageous Effect of Invention

The microfluidic device according to present disclosure can reduce a fluctuation in reaction time of the reaction solution flowing through the flow path, and can perform a reaction of a reaction solution flowing through a flow path in a reaction time close to a predetermined reaction time.

DESCRIPTION OF EXEMPLARY EMBODIMENTS

Figure 1:
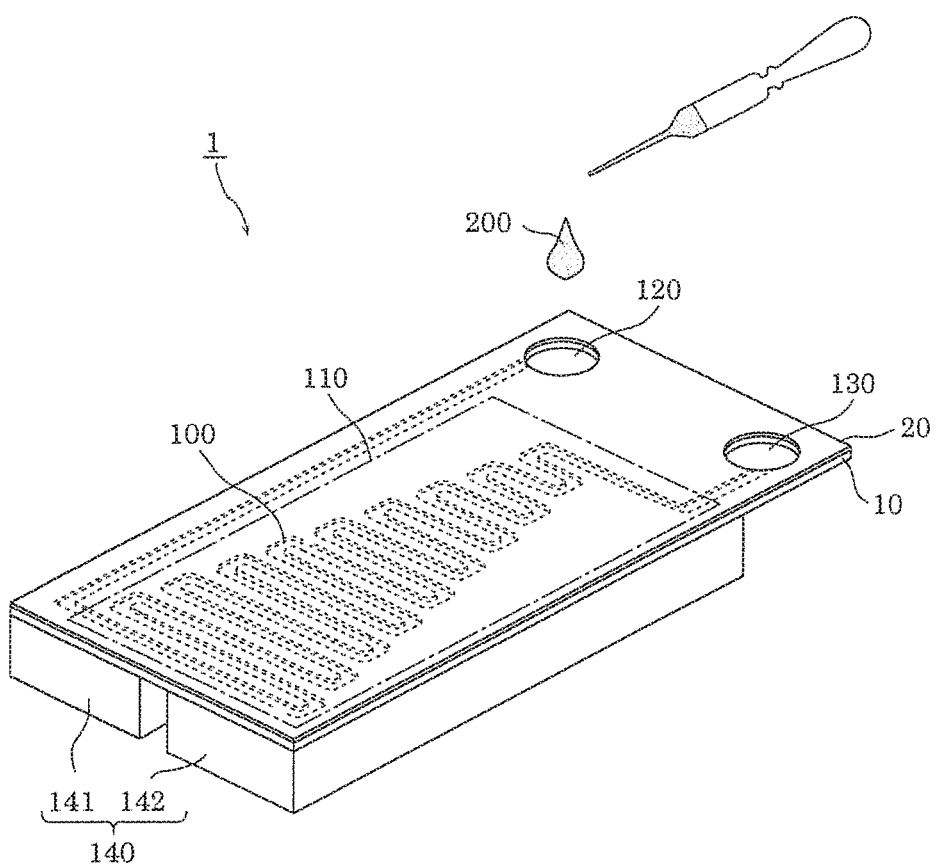
FIG. 1 is a perspective view illustrating a schematic configuration of a microfluidic device according to Embodiment 1.

The embodiments according to present disclosure will now be described with reference to the drawings. The embodiments to be described below only show specific examples of the present disclosure. Accordingly, numeral values, shapes, materials, components, arrangements, positions, and connection forms of the components, steps, order of the steps, and the like shown in the embodiments below are only examples, and will not limit the present disclosure. Accordingly, among the components of the embodiments below, the components not described in an independent claim representing the most superordinate concept of the present disclosure are described as optional components.

The drawings are schematic views, and are not always strict illustrations. In the drawings, identical reference numerals are given to substantially identical configurations, and the duplication of description will be omitted or simplified.

Embodiment 1

Schematic Configuration of Microfluidic Device

Figure 2:
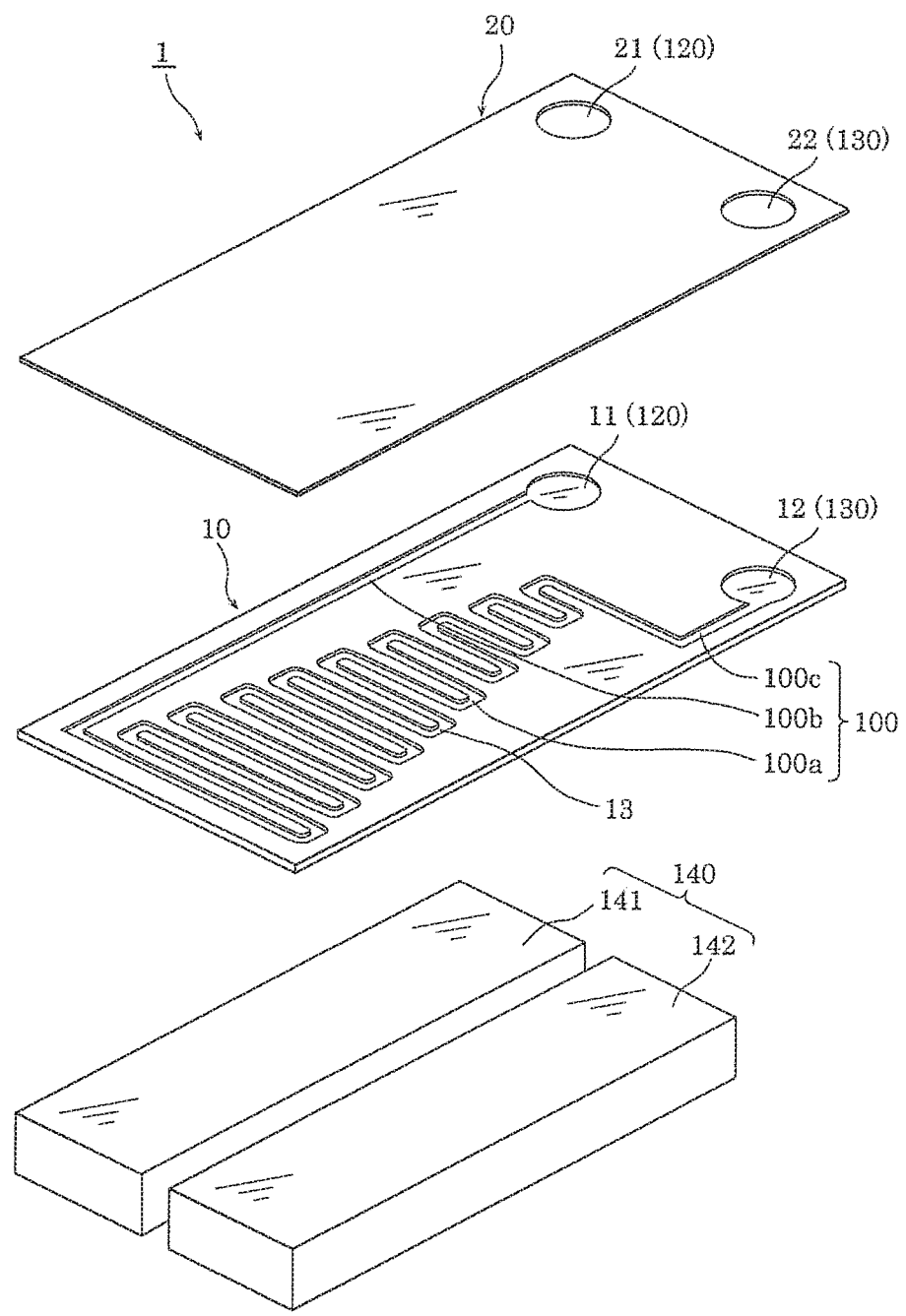
FIG. 2 is an exploded perspective view illustrating a microfluidic device according to Embodiment 1.
Figure 3:
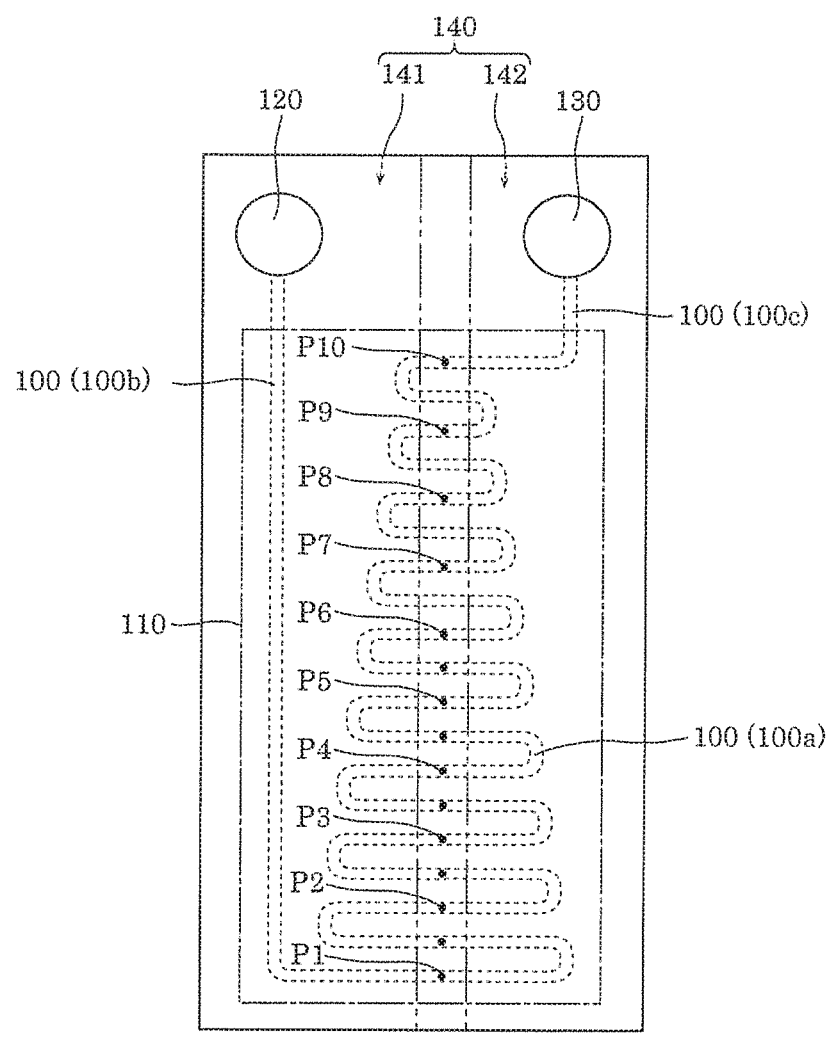
FIG. 3 is a plan view illustrating the microfluidic device according to Embodiment 1.

The configuration of microfluidic device 1 according to Embodiment 1 will be described with reference to FIGS. 1 to 3. FIG. 1 is a perspective view illustrating a schematic configuration of microfluidic device 1 according to Embodiment 1. FIG. 2 is an exploded perspective view of microfluidic device 1. FIG. 3 is a plan view of microfluidic device 1.

Microfluidic device 1 is a device (microflow path chip) including flow path 100 through which reaction solution 200 flows, reaction portion 110 for reacting reaction solution 200 flowing through flow path 100, introducing portion 120 for introducing reaction solution 200 into flow path 100, and discharging portion 130 for discharging reaction solution 200.

Flow path 100 is disposed, at least, to pass through reaction portion 110. In the present embodiment, reaction solution 200 introduced into flow path 100 is fed through flow path 100 by capillary action (capillary force). For example, feeding of reaction solution 200 by capillary force can be achieved by flow path 100 having hydrophilic inner surfaces having a sharp contact angle.

Flow path 100 is a one-way reaction flow path for reaction solution 200, and is formed as a single flow path. One end of flow path 100 is connected to introducing portion 120, and the other end thereof is connected to discharging portion 130. In other words, one end of flow path 100 is introducing portion 120, and the other end of flow path 100 is discharging portion 130.

Flow path 100 passes through reaction portion 110. Although the details will be described later, flow path 100 is configured to pass alternately and repeatedly several times through a first temperature region and a second temperature region having different predetermined temperatures.

Furthermore, the repeating unit portions in a first temperature region and a second temperature region of flow path 100 have decreasing lengths (flow path length for each temperature cycle) as the repeating unit portions are located farther away from introducing portion 120 along the solution feeding direction of reaction solution 200. In other words, the repeating unit portion passing through the first temperature region and the second temperature region in flow path 100 is shorter as the repeating unit portion is located closer to the side downstream of the solution feeding direction.

As illustrated in FIGS. 2 and 3, in the present embodiment, flow path 100 includes three flow path sections, i.e., main flow path 100a disposed in reaction portion 110, introducing flow path 100b for guiding reaction solution 200 from introducing portion 120 to reaction portion 110, and discharging flow path 100c for guiding reaction solution 200 from reaction portion 110 to discharging portion 130.

As illustrated in FIG. 3, main flow path 100a is a serpentine flow path such that the flow path meanders, and has a plurality of turns as bonded portions. Main flow path 100a is formed (in a reciprocating manner) such that a linear flow path is bent at predetermined intervals to continuously turn. In other words, main flow path 100a is bent corresponding to a plurality of cycles such that main flow path 100a travels through the first temperature region and the second temperature region having different temperatures in a reciprocating manner. Main flow path 100a includes a plurality of linear portions (straight line portions), and a plurality of bent portions (turns) connecting the linear portions. The number of turns in main flow path 100a is about 20 to 70 cycles, for example. FIG. 3 illustrates only about 10 cycles.

Reaction portion 110 is a region for reacting reaction solution 200 introduced into microfluidic device 1. Reaction portion 110 includes at least two or more temperature regions having different predetermined temperatures.

Reaction solution 200 (reaction fluid) contains a sample of a target nucleic acid, for example. Specifically, reaction solution 200 is an aqueous solution containing a target nucleic acid and a reaction reagent for amplifying the target nucleic acid, for example. Accordingly, reaction portion 110 in the present embodiment is a nucleic acid amplification reaction portion. The target nucleic acid contained in reaction solution 200 is amplified in reaction portion 110. Reaction solution 200 may contain alcohol or a surfactant.

Introducing portion 120 is a sample inlet from which reaction solution 200 containing a sample of a target nucleic acid is introduced. Introducing portion 120 is the start point of flow path 100. In other words, introducing portion 120 serves as a feeding start point for reaction solution 200.

Discharging portion 130 is a sample outlet (drain) for discharging reaction solution 200 containing the target nucleic acid amplified in reaction portion 110. Discharging portion 130 is the end point of flow path 100. In other words, discharging portion 130 is the feeding end point for reaction solution 200. Reaction solution 200 is optionally not discharged from discharging portion 130.

Thus, microfluidic device 1 according to the present embodiment is used as a nucleic acid amplification device for amplifying a sample of a target nucleic acid. As one example, a case where a polymerase chain reaction (PCR) is performed using microfluidic device 1 will be described.

PCR is a technique of amplifying target DNA through temperature cycling. In this case, the reaction solution contains the target DNA, as well as a PCR primer, a polymerase enzyme, and a buffer. The target DNA can be amplified through temperature cycling of such a reaction solution. The amount of the amplified DNA can be detected by a reaction detecting mechanism. In the present embodiment, the reaction solution passes through flow path 100, and as a result, the target nucleic acid contained in the reaction solution is amplified by PCR.

Flow path 100 (main flow path 100a) disposed in reaction portion 110 passes through at least two or more temperature regions having different predetermined temperatures in a reciprocating manner in a plurality of cycles. Reaction solution 200 flowing through main flow path 100a is subjected to temperature cycling by heater 140. The two or more temperature regions include a first temperature region (low temperature region) having a first temperature, and a second temperature region (high temperature region) having a second temperature higher than the first temperature. Specifically, main flow path 100*a* passes alternately and repeatedly through the low temperature region (first heater block 141) and the high temperature region (second heater block 142).

Furthermore, in main flow path 100*a*, the repeating unit portions passing through the first temperature region (low temperature region) corresponding to first heater block 141 and the second temperature region (high temperature region) corresponding to second heater block 142 have gradually decreasing lengths as the repeating unit portions are located farther away from introducing portion 120. In other words, the repeating unit portion passing through the first temperature region (low temperature region) and the second temperature region (high temperature region) is longer as the repeating unit portion is located closer to introducing portion 120, and the repeating unit portion is shorter as the repeating unit portion is located closer to discharging portion 130. The repeating unit passing through the first temperature region (low temperature region) and the second temperature region (high temperature region) is a repeating unit corresponding to each of the PCR cycles. For example, in FIG. 3, the repeating units passing through the first temperature region and the second temperature region correspond to one cycle length from P1 to P2 of main flow path 100*a*, one cycle length from P2 to P3 of main flow path 100*a*, . . . , and one cycle length from P9 to P10 of main flow path 100*a*, respectively.

In the present embodiment, such repeating units corresponding to the PCR cycles and having decreasing lengths away from introducing portion 120 are implemented by varying the length of the repeating unit in the serpentine flow path of main flow path 100*a*. In other words, the length of the repeating unit portion (flow path length) of the serpentine flow path is increased along the solution feeding direction of reaction solution 200 as the repeating unit portion is located closer to introducing portion 120, and is decreased along the solution feeding direction of reaction solution 200 as the repeating unit portion is located closer to discharging portion 130.

Specifically, in main flow path 100*a* forming the serpentine flow path, the repeating unit is defined by part of main flow path 100*a* traveling from one of the first temperature region (low temperature region) and the second temperature region (high temperature region) to the other. In the present embodiment, the repeating unit is defined by the linear portion of main flow path 100*a* in FIG. 3. In other words, in the present embodiment, the length of the repeating unit portion passing through the first temperature region and the second temperature region in main flow path 100*a* corresponds to the length of the linear portion (flow path length) between adjacent two turns in main flow path 100*a*. Accordingly, the length of the linear portion (length of the linear portion between adjacent two turns sandwiching the linear portion) of main flow path 100*a* is shorter as the linear portion is located farther away from introducing portion 120.

In main flow path 100*a*, portions of the repeating unit portions which pass through the first temperature region and portions of the repeating unit portions which pass through the second temperature region have decreasing lengths as these repeating unit portions are located farther away from introducing portion 120, but the configuration is not limited to this. For example, of the length of the repeating unit portion in the first temperature region and that of the second temperature region, one may be fixed, and the other may be decreased as these repeating unit portions are located farther away from introducing portion 120.

Although reaction portion 110 in the present embodiment has main flow path 100*a* in which the length of the repeating unit portion in the first temperature region and that in the second temperature region are gradually decreased toward discharging portion 130, flow path 100 may partially include intermediate portions in which two adjacent repeating units have the same flow path length or one of the adjacent repeating units is slightly longer than the other. In other words, it is sufficient that main flow path 100*a*, as a whole, has a tendency that the repeating unit portions passing through the first temperature region and the second temperature region in main flow path 100*a* have decreasing lengths toward discharging portion 130.

Specific components included in microfluidic device 1 will now be described in more detail with reference to FIGS. 1 to 3.

As illustrated in FIGS. 1 and 2, microfluidic device 1 includes first substrate 10, second substrate 20, and heater 140. Microfluidic device 1 may include first substrate 10 and second substrate 20 without heater 140.

First Substrate

As illustrated in FIG. 2, first substrate 10 includes first depression 11 forming part of introducing portion 120, second depression 12 forming part of discharging portion 130, and groove 13 forming flow path 100.

First substrate 10 to be used can be a resin substrate made of poly(ethylene terephthalate) (PET), polycarbonate (PC), cycloolefin polymer (COP), or acrylic resin, for example.

First depression 11 and second depression 12 are circular openings, for example. Reaction solution 200 flows through groove 13. In other words, groove 13 forms flow path 100. Specifically, groove 13 includes main flow path 100*a*, introducing flow path 100*b*, and discharging flow path 100*c*, and is formed so as to connect first depression 11 to second depression 12. Such a configuration allows reaction solution 200 introduced into first depression 11 (introducing portion 120) to travel through groove 13 (flow path 100) to second depression 12 (discharging portion 130).

In the present embodiment, groove 13 corresponding to main flow path 100*a* has hydrophilic inner surfaces. Specifically, the inner surfaces of groove 13 corresponding to main flow path 100*a* are surface treated with a surfactant to be hydrophilic. For example, the bottom surface and the side surfaces of groove 13 can be hydrophilicized through coating with a surfactant to form a hydrophilic film on the inner surfaces of groove 13. Groove 13 corresponding to introducing flow path 100*b* and discharging flow path 100*c* has hydrophilic inner surfaces as main flow path 100*a* has.

Flow path 100 is a microflow path having a width in the order of micrometers. In the present embodiment, flow path 100 has a fixed width. Specifically, groove 13 including main flow path 100*a*, introducing flow path 100*b*, and discharging flow path 100*c* has a rectangular cross-section, and has a fixed width and depth. Flow path 100 (groove 13) may have a varying width and depth.

As an example, groove 13 including main flow path 100*a*, introducing flow path 100*b*, and discharging flow path 100*c* has a flow path width (width of the groove) of 50 to 500 µm, a depth of 50 to 150 µm, and a flow path length of 500 to 3000 mm. The flow path width, depth, and flow path length of flow path 100 (groove 13) are not limited to these ranges.

First substrate 10 is not limited to the resin substrate, and may be a glass substrate or a silicon substrate. Use of a silicon substrate as the first substrate can facilitate formation of a silicon oxide film on the inner surfaces of groove 13 forming main flow path 100*a*. Since the silicon oxide film has hydrophilicity, the inner surfaces of main flow path 100*a* can be hydrophilicized through formation of a silicon oxide film on the wall surfaces (inner surfaces) of main flow path 100a (groove 13). First substrate 10 may be one of a translucent substrate (such as a transparent substrate) and a non-translucent substrate. Groove 13 can have any cross-sectional shape other than a rectangular shape, such as a semi-circular or inverted triangular shape.

Second Substrate

As illustrated in FIG. 1, second substrate 20 is a lid covering first substrate 10, and is disposed on first substrate 10. Second substrate 20 to be used can be a transparent resin substrate or a glass substrate, for example.

As illustrated in FIG. 2, second substrate 20 includes first through hole 21 as part of introducing portion 120. First through hole 21 penetrates through second substrate 20. Second substrate 20 includes second through hole 22 as part of discharging portion 130. Second through hole 22 penetrates through second substrate 20. First through hole 21 and second through hole 22 are circular openings.

Second substrate 20 is placed on first substrate 10 to cover the openings of groove 13 in first substrate 10, defining flow path 100 sealed in all directions. In such a configuration, flow path 100 has closed wall surfaces in cross-sections vertical to the solution feeding direction (traveling direction) of reaction solution 200 (the flow path is covered with walls in four directions), and is connected to an external space through introducing portion 120 and discharging portion 130. Thus, flow path 100 sealed all around can enhance the capillary force of flow path 100, and prevent volatilization of reaction solution 200 during feeding thereof.

Second substrate 20 is not limited to the resin substrate or a glass substrate, and may be a silicon substrate. Second substrate 20 may be a substrate not transparent.

Heater

Heater 140 is a heating device for heating reaction solution 200 flowing through flow path 100. Heater 140 is disposed at least corresponding to reaction portion 110. Reaction solution 200 fed to flow path 100 (main flow path 100a) of reaction portion 110 is heated to a predetermined temperature by heater 140.

Heater 140 includes first heater block 141 and second heater block 142 having different setting temperatures. Accordingly, first heater block 141 and second heater block 142 are disposed corresponding to reaction portion 110. In other words, reaction portion 110 has two temperature regions set at different predetermined temperatures by the two heater blocks, i.e., first heater block 141 and second heater block 142.

First heater block 141 and second heater block 142 are cuboid block heaters made of a metal such as aluminum or stainless steel. Examples of heater 140 which can be used include heater blocks, and metal thin film heaters obtained by forming a metal thin film on a glass substrate by printing.

In the present embodiment, the temperature (second temperature) of second heater block 142 is set to be higher than the temperature (first temperature) of first heater block 141. In other words, the region in which second heater block 142 is disposed is a high temperature region, and the region in which first heater block 141 is disposed is a low temperature region.

The temperature of first heater block 141 corresponding to the low temperature region is, for example, 50° C. to 75° C., and about 60° C. in the present embodiment, which is a temperature for annealing and extension reactions. The temperature of second heater block 142 corresponding to the high temperature region is, for example, 93° C. to 98° C., and is about 95° C. in the present embodiment, which is a temperature for denaturation reaction in a nucleic acid amplification reaction.

Heater 140 is connected to a temperature control unit (not illustrated). Thus, the temperatures of first heater block 141 and second heater block 142 can be controlled by the temperature control unit.

First heater block 141 and second heater block 142 are aligned at a predetermined interval. First substrate 10 is disposed on first heater block 141 and second heater block 142. Specifically, first substrate 10 is placed on heater 140 such that main flow path 100a in flow path 100 alternately travels above first heater block 141 and second heater block 142. Thus, main flow path 100a is configured to travel through the two temperature regions in a reciprocating manner in a plurality of cycles. In other words, main flow path 100a passes alternately and repeatedly through first heater block 141 (low temperature region) and second heater block 142 (high temperature region).

Characteristics of Microfluidic Device

The characteristics of microfluidic device 1 including the development of the present disclosure will now be described.

Figure 4:
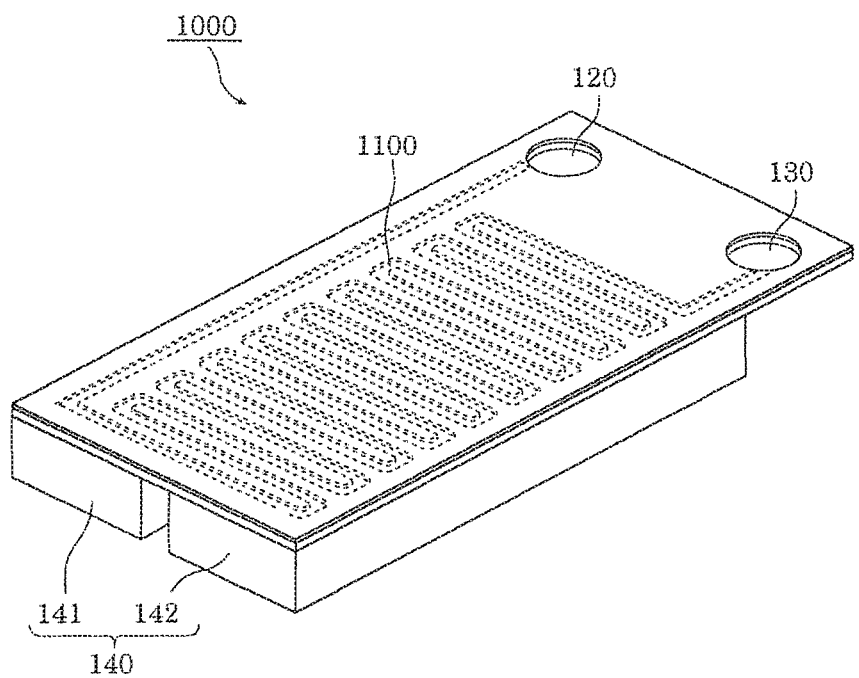
FIG. 4 is a perspective view illustrating a schematic configuration of a conventional microfluidic device.

FIG. 4 is a perspective view illustrating a schematic configuration of conventional microfluidic device 1000.

As illustrated in FIG. 4, similarly to flow path 100 of microfluidic device 1 in Embodiment 1, flow path 1100 in conventional microfluidic device 1000 is a serpentine flow path which passes alternately and repeatedly several times through a first temperature region and a second temperature region having different temperatures. Unlike flow path 100 of microfluidic device 1 in the Embodiment 1, the first temperature region and the second temperature region in flow path 100 have a fixed length of the repeating unit portion (flow path length for temperature cycling).

Conventional microfluidic device 1000 also feeds the reaction solution by capillary force as in microfluidic device 1 in Embodiment 1.

Figure 5:
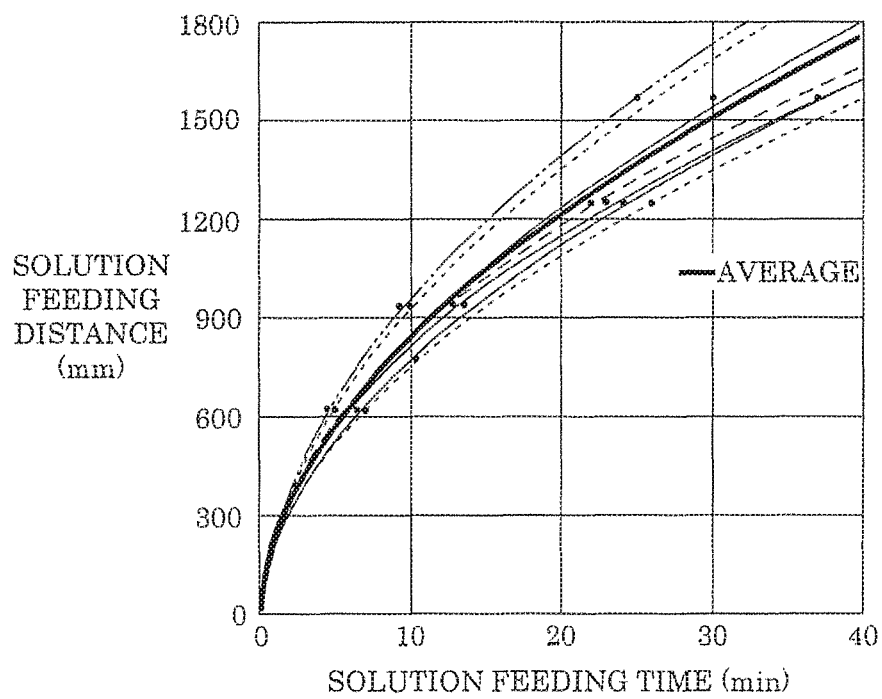
FIG. 5 is a graph illustrating the relationship between the solution feeding distance of the reaction solution flowing through the flow path and the solution feeding time thereof.

In this case, in the relation between the solution feeding distance and the solution feeding time of the reaction solution flowing through flow path 1100 as illustrated in FIG. 5, a longer solution feeding distance results in a longer solution feeding time. However, the solution feeding distance of the reaction solution is not proportional with the solution feeding time thereof. As the solution feeding distance is longer, the solution feeding time per unit solution feeding distance is gradually longer. In other words, as the solution feeding distance is longer, the solution feeding distance per unit solution feeding time is shorter. In other words, it indicates that as the solution feeding distance is longer, the solution feeding rate is gradually lower. It is believed that this is because the resistance of the inner walls of flow path 1100 increases, gradually reducing the rate.

As a result, the reaction solution flows faster near the feeding start point of flow path 100 (near introducing portion 120) because of a high solution feeding rate, and flows slower because the solution feeding rate gradually reduces toward the feeding end point (discharging portion 130).

Microfluidic device 1000 has such a fluctuation in solution feeding rate of the reaction solution flowing through flow path 1100. Specifically, the solution feeding rate of the reaction solution near the start point is different from that near the end point of flow path 1100.

As a result, flow path 1100 has different reaction times near the start point and near the end point, inhibiting a uniform reaction of the reaction solution through the entire flow path. If a sufficient reaction time near the start point is ensured to sufficiently perform a nucleic acid amplification reaction, the reaction time near the end point is increased beyond necessity, increasing the time to complete the feeding of the solution.

The present inventors, who have conducted extensive research about a method for preventing a fluctuation in solution feeding rate of the reaction solution, have found that the reaction rate of the solution feeding near the feeding start point can be brought close to the reaction rate near the feeding end point through adjustment of the length of the repeating unit portion passing through the first temperature region and the second temperature region in the flow path.

Specifically, as illustrated in FIGS. 1 and 3, flow path 100 is configured to pass alternately and repeatedly several times through the first temperature region and the second temperature region having different predetermined temperatures. In such a flow path, the repeating unit portions passing through the first temperature region and the second temperature region have decreasing lengths (flow path lengths) along the solution feeding direction of reaction solution 200 as the repeating unit portions are located farther away from introducing portion 120.

Figure 6:
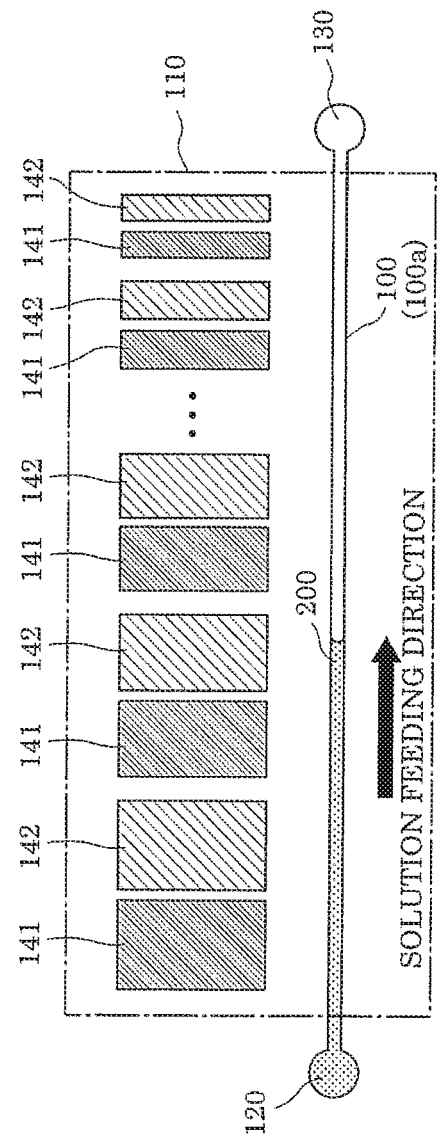
FIG. 6 is a diagram illustrating exemplary temperature cycling of the microfluidic device according to Embodiment 1.

The characteristics of microfluidic device 1 according to the present embodiment will now be described with reference to FIGS. 1 to 3, and FIG. 6. FIG. 6 is a diagram illustrating temperature cycling of microfluidic device 1 according to Embodiment 1. In the present embodiment, a case where microfluidic device 1 is used as a nucleic acid amplification device will be described.

First, a sample, i.e., the target nucleic acid and a reaction reagent for amplifying the target nucleic acid are introduced into introducing portion 120 of microfluidic device 1. For example, a pre-mixed solution of a reaction solution containing the target nucleic acid and a reaction reagent is prepared as reaction solution 200, and is injected into introducing portion 120 using a pipette as illustrated in FIG. 1.

Reaction solution 200 introduced into introducing portion 120 is fed from introducing portion 120 through flow path 100 to reaction portion 110. Specifically, reaction solution 200 flows through introducing flow path 100b, and is fed to main flow path 100a of reaction portion 110.

In reaction portion 110, reaction solution 200 is subjected to a cyclic change in temperature. As a result, the target nucleic acid contained in reaction solution 200 is amplified.

Specifically, as illustrated in FIG. 6, reaction solution 200 reaching reaction portion 110 passes through flow path 100 (main flow path 100a) in a repeating and reciprocating manner between first heater block 141 and second heater block 142. In other words, since reaction solution 200 is fed such that reaction solution 200 alternately and repeatedly travels through the two temperature regions, i.e., the low temperature region (first heater block 141) and the high temperature region (second heater block 142) in reaction portion 110 in sequence, the reaction solution is alternately and repeatedly heated and cooled. Thereby, reaction solution 200 flowing through flow path 100 (main flow path 100a) is subjected to heat cycling; thus, the target nucleic acid contained in reaction solution 200 is amplified through repetition of the denaturation at the high temperature region and the annealing and extension at the low temperature region.

Such heating and cooling of reaction solution 200 during feeding can achieve extremely high-speed flow PCR. Accordingly, the target nucleic acid contained in reaction solution 200 can be amplified at high speed.

In this case, in the present embodiment, as illustrated in FIG. 3, the repeating unit portions passing through the first temperature region and the second temperature region having different setting temperatures in flow path 100 have decreasing lengths along the solution feeding direction of reaction solution 200 as the repeating unit portions are located farther away from introducing portion 120.

In other words, as illustrated in FIG. 6, the length of the repeating unit portion passing through the first temperature region (region corresponding to first heater block 141) and the second temperature region (region corresponding to second heater block 142) in flow path 100 is longer as the repeating unit portion is located closer to the feeding start point (nearer introducing portion 120) having a higher solution feeding rate, and is gradually shorter toward the feeding end point (nearer discharging portion 130) having a lower solution feeding rate.

Thus, reaction portion 110 has a small fluctuation in time of reaction solution 200 present in the respective repeating unit portions passing through the first temperature region and the second temperature region in flow path 100. Accordingly, the reaction time of reaction solution 200 can be closer to a predetermined time across reaction portion 110.

As a result, reaction solution 200 can be uniformly reacted across the flow path. An excess reaction time near the end point can be eliminated in the case where a sufficient reaction time is ensured near the start point to sufficiently amplify the nucleic acid, therefore reducing the time until the feeding of the reaction solution is completed.

It should be noted that in FIG. 6, first heater block 141 and second heater block 142 are not illustrated in actual sizes (widths), and the flow path length of flow path 100 (main flow path 100a) passing through these heater blocks is schematically illustrated.

In microfluidic device 1 according to the present embodiment, reaction solution 200 is thus fed from introducing portion 120 to discharging portion 130.

The introduction of reaction solution 200 into introducing portion 120 is stopped when the tip of the flow of reaction solution 200 has reached discharging portion 130; then, reaction solution 200 is fed across flow path 100, and flow path 100 is filled with reaction solution 200.

In the present embodiment, reaction solution 200, when traveling through flow path 100, is fed through flow path 100 by capillary force. For example, hydrophilic inner surfaces of flow path 100 (main flow path 100a, introducing flow path 100b, and discharging flow path 100c) enable feeding of reaction solution 200 by capillary force. Reaction solution 200 is thus fed as a self-propelled flow through flow path 100 by the capillary force generated at the gas-liquid interface, and therefore automatically travels through flow path 100.

Accordingly, the target nucleic acid contained in reaction solution 200 is amplified in reaction portion 110 while reaction solution 200 is being fed through flow path 100 (main flow path 100a) by the capillary force. In other words, the target nucleic acid is amplified by cyclically varying the temperature of reaction solution 200 in reaction portion 110 while automatically delivering reaction solution 200 in flow path 100.

At least part of the wall surfaces of flow path 100 (main flow path 100a, introducing flow path 100b, and discharging flow path 100c) are hydrophilic. It is better, however, that the entire wall surfaces of flow path 100 in the cross-sections vertical to the solution feeding direction are hydrophilic. In this case, hydrophilic surfaces should be formed not only in the surfaces of groove 13 of first substrate 10 but also in the surfaces (inner surfaces) of second substrate 20. A larger proportion of the hydrophilic wall surface in the cross-sections of flow path 100 can increase the capillary force to reaction solution 200.

After reaction solution 200 is fed across flow path 100, the amount of amplification of the target nucleic acid contained in reaction solution 200 is detected. In this case, for example, the amount of amplification of the target nucleic acid is detected using an optical detector. Specifically, an optical detector scans main flow path 100a in reaction portion 110 with laser light in a direction intersecting the linear portions, and receives reflected light. Based on the received reflected light, the optical detector calculates the amount of amplification of the target nucleic acid in the reaction solution in main flow path 100a.

Thereby, an amplification curve of the nucleic acid according to the cycles of main flow path 100a formed by reciprocation between first heater block 141 and second heater block 142 can be obtained. In other words, the amount of amplification of the nucleic acid at each cycle of main flow path 100a can be detected as an amplification curve through scanning of main flow path 100a with laser light. Specifically, an amplification curve is obtained in which the amount of amplification of the nucleic acid increases with an increase in PCR cycles.

In one example, the optical detector can be configured such that the reaction solution is irradiated with blue laser light as excitation light, and green fluorescent light exited by the blue laser light and emitted from the reaction solution by the blue laser light is returned as reflected light. The intensity of this green fluorescent light (reflected light) varies according to the amount of amplification of the nucleic acid. Accordingly, the amount of amplification of the nucleic acid can be calculated based on the measured intensity of this green fluorescent light.

SUMMARY

As described above, in microfluidic device 1 according to the present embodiment, the repeating unit portions passing through the first temperature region and the second temperature region having different predetermined temperatures in flow path 100 have decreasing lengths along the feeding direction of reaction solution 200 as the repeating unit portions are located farther away from introducing portion 120.

Such a configuration can reduce a fluctuation in reaction time of reaction solution 200 flowing through flow path 100, and therefore can provide a microfluidic device which can perform a reaction of reaction solution 200 in reaction portion 110 in a reaction time close to a predetermined reaction time. Accordingly, a constant reaction time of reaction solution 200 can be provided across flow path 100 in reaction portion 110.

Moreover, in the present embodiment, reaction solution 200 is fed through flow path 100 by capillary force.

Such capillary feeding of reaction solution 200 results in the difference in the solution feeding rate of reaction solution 200 between a portion near the start point of flow path 100 and a portion near the end point thereof. However, in the present embodiment, the difference in the solution feeding rate between a portion near the start point of flow path 100 and a portion near the end point thereof can be absorbed by the configuration of the first temperature region and the second temperature region in which the repeating unit portions in flow path 100 have decreasing lengths as the repeating unit portions are located farther away from introducing portion 120. In other words, even if the solution feeding rate of a portion near the start point is different from that of a portion near the end point, reaction solution 200 in reaction portion 110 can be reacted in the reaction time closer to a predetermined reaction time.

Figure 7:
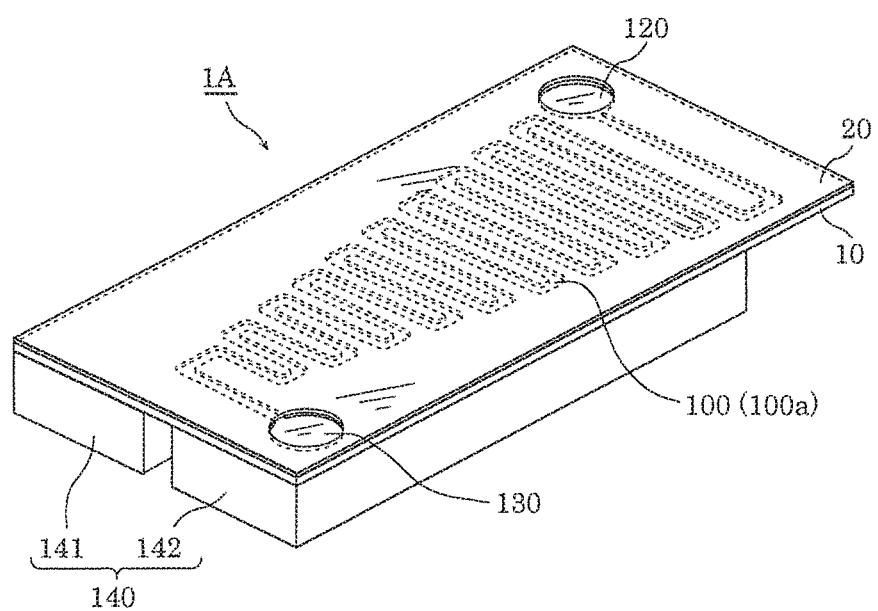
FIG. 7 is a perspective view illustrating a schematic configuration of a microfluidic device according to Modification 1 of Embodiment 1.

Although introducing portion 120 and discharging portion 130 are disposed at one end of microfluidic device 1 in the present embodiment, introducing portion 120 (start point) and discharging portion 130 (end point) may be disposed at different positions and/or different ends of the microfluidic device. For example, as illustrated in FIG. 7, introducing portion 120 may be disposed at one end of microfluidic device 1A, and discharging portion 130 may be disposed at the other end of microfluidic device 1A.

In the present embodiment, main flow path 100a is a serpentine flow path, but main flow path 100a may have any shape. For example, as illustrated in microfluidic device 1B in FIG. 8, main flow path 100a may be a linear flow path. In this case, to provide decreasing repeating unit portions passing through the first temperature region and the second temperature region in main flow path 100a as the repeating unit portions are located farther away from introducing portion 120, a plurality of first heater blocks 141 (first temperature regions) and a plurality of second heater blocks 142 (second temperature regions) are formed to have decreasing lengths (widths) in the solution feeding direction as these blocks are located farther away from introducing portion 120.

However, a serpentine flow path illustrated in FIG. 3 can ensure longer increasing flow path lengths for main flow path 100a in a smaller space, thus achieving a smaller microfluidic device. Use of only a repeatedly reciprocating serpentine flow path and single first heater block 141 and single second heater block 142 can provide main flow path 100a including a plurality of repeating unit portions passing through the first temperature region and the second temperature region in main flow path 100a. Such a configuration can achieve heater 140 having a simple structure.

Figure 8:
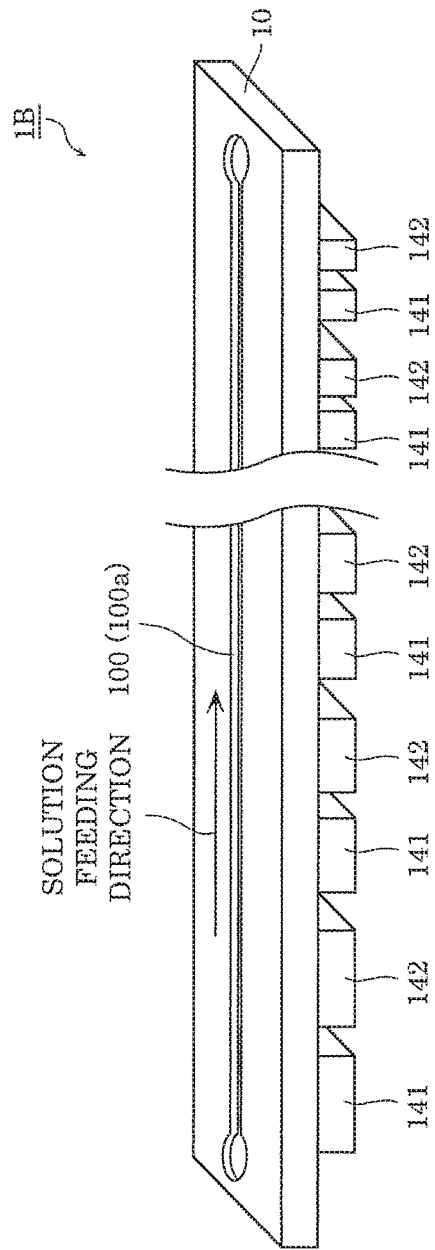
FIG. 8 is a perspective view illustrating a schematic configuration of a microfluidic device according to Modification 2 of Embodiment 1.

Although second substrate 20 is not illustrated in FIG. 8, second substrate 20 may be disposed on first substrate 10.

Embodiment 2

Figure 9:
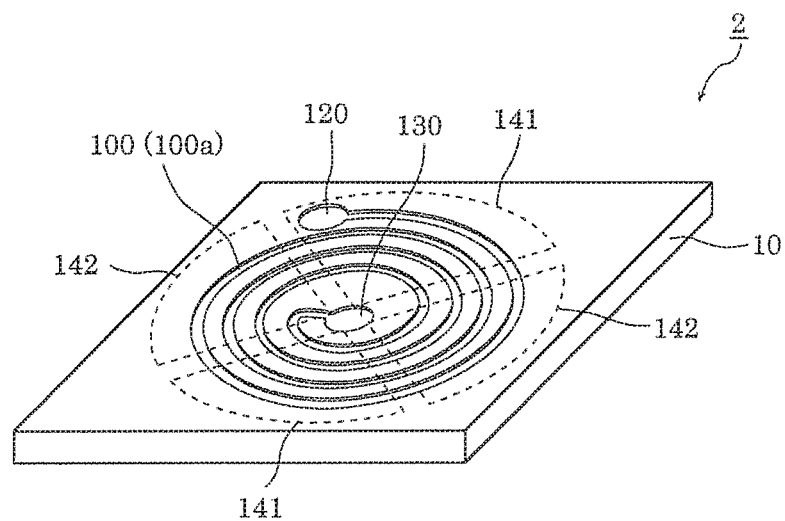
FIG. 9 is a perspective view illustrating a schematic configuration of a microfluidic device according to Embodiment 2.

A schematic configuration of microfluidic device 2 according to Embodiment 2 will now be described with reference to FIG. 9. FIG. 9 is a perspective view illustrating a schematic configuration of microfluidic device 2 according to Embodiment 2. Although second substrate 20 is not illustrated in FIG. 9, second substrate 20 may be disposed on first substrate 10 as in Embodiment 1. Although heater 140 is not illustrated in FIG. 9, heaters 140 (first heater block 141 and second heater block 142) having a predetermined shape are disposed on the rear side of first substrate 10.

As illustrated in FIG. 9, microfluidic device 2 includes spiral flow path 100 in a plan view. In the present embodiment, flow path 100 is disposed in the form of an approximately circular spiral in a plan view. Specifically, flow path 100 is disposed in the form of connected arcs having different diameters. The arcs include those of perfect circles and those of ellipses.

Flow path 100 (main flow path 100a) includes introducing portion 120 at one end thereof, and introducing portion 120 is located on the outermost side of the spiral. Flow path 100 (main flow path 100a) includes discharging portion 130 disposed at the other end thereof, and discharging portion 130 is located on the innermost side of the spiral. In the present embodiment, discharging portion 130 is disposed at the center of the spiral.

First substrate 10 includes first heater block 141 and second heater block 142 on the rear side thereof. First heater block 141 and second heater block 142 both have a shape of a sector in a plan view. In the present embodiment, two first heater blocks 141 and two second heater blocks 142 are disposed. Each of first heater blocks 141 and second heater blocks 142 has a shape corresponding to a quarter of a circle divided by two straight lines passing through the center of the circle. First heater blocks 141 and second heater blocks 142 are alternated along the circumferential direction of the spiral.

As described above, in the present embodiment, flow path 100 has a spiral shape, and includes introducing portion 120 on the outermost side of the spiral and discharging portion 130 on the innermost side of the spiral. Spiral flow path 100 has an increasing flow path length (arc) toward the outside thereof, and a decreasing flow path length (arc) toward the inside thereof.

The configuration according to the present embodiment also can achieve decreasing lengths of the repeating unit portions passing through the first temperature region (region corresponding to first heater block 141) and the second temperature region (region corresponding to second heater block 142) having different predetermined temperatures in flow path 100 as the repeating unit portions are located farther away from introducing portion 120.

As a result, the repeating unit portions passing through the first temperature region (region corresponding to first heater block 141) and the second temperature region (region corresponding to second heater block 142) in flow path 100 can have increasing lengths as the repeating unit portions are located closer to the feeding start point (nearer introducing portion 120) having a higher solution feeding rate, and can have decreasing lengths as the repeating unit portions are located closer to the feeding end point (nearer discharging portion 130) having a lower solution feeding rate.

Accordingly, the reaction solution flowing through flow path 100 can be reacted in the reaction time closer to a predetermined reaction time. As a result, the reaction solution can be uniformly reacted across the flow path. Moreover, the feeding of the reaction solution can be completed faster near the end point of the flow path having a low solution feeding rate.

A serpentine flow path such as flow path 100 included in microfluidic device 1 according to Embodiment 1 has sharp turns to decelerate the reaction solution, and thus cannot feed the reaction solution at a constant rate. In contrast, spiral flow path 100 in the present embodiment has no sharp turns, and thus can feed the reaction solution at a constant rate.

Microfluidic device 2 according to the present embodiment also has a structure in which the reaction solution is fed by capillary force, but microfluidic device 2 can have any other structure.

Microfluidic device 2 according to the present embodiment includes flow path 100 disposed in the form of an approximately circular spiral, but the flow path may be disposed in any other form.

Figure 10:
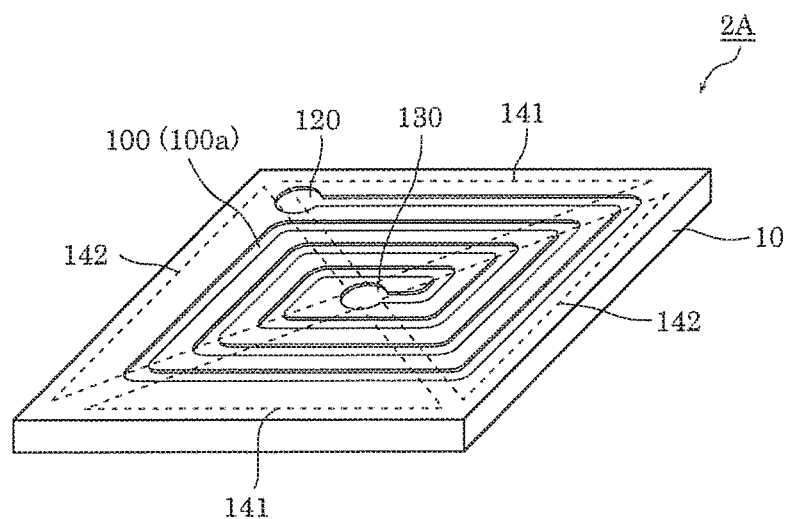
FIG. 10 is a perspective view illustrating a schematic configuration of a microfluidic device according to Modification 1 of Embodiment 2.

For example, as in microfluidic device 2A illustrated in FIG. 10, flow path 100 may be disposed in the form of an approximately square spiral in a plan view. In other words, the spiral may be formed with a plurality of linear flow paths having different lengths and sequentially connected to one another so as to make an angle of 90 degrees. In this case, the reaction solution flowing through flow path 100 can be reacted in the reaction time closer to a predetermined reaction time as in microfluidic device 2 according to Embodiment 2.

Moreover, flow path 100 includes turns having an angle of approximately 90 degrees in microfluidic device 2A illustrated in FIG. 10. For this reason, compared to the serpentine flow path having sharp turns, the deceleration of the reaction solution at turns can be relaxed.

In addition, flow path 100 has a linear shape in the first temperature region (first heater block 141) and the second temperature region (second heater block 142). For this reason, compared to spiral flow path 100 illustrated in FIG. 9, the reaction solution can be reacted in a desired manner.

Furthermore, compared to flow path 100 disposed in an approximately circular spiral form, flow path 100 disposed in the form of an approximately square spiral can lead to a more efficient arrangement of flow path 100 in first substrate 10, thus providing a device having a smaller area.

In microfluidic device 2A illustrated in FIG. 19, first heater block 141 and second heater block 142 have a shape corresponding to a quarter of a square divided by lines passing through discharging portion 130 as the center, but these heater blocks may have any other shape.

Figure 11:
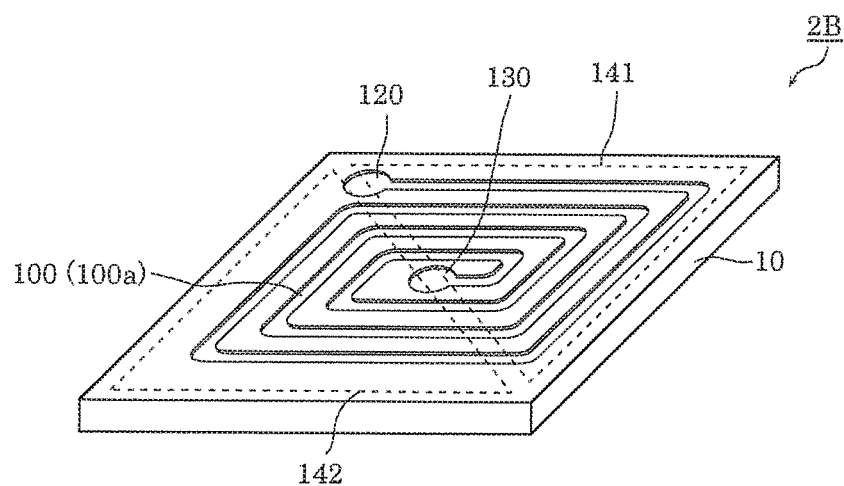
FIG. 11 is a perspective view illustrating a schematic configuration of a microfluidic device according to Modification 2 of Embodiment 2.

For example, as in microfluidic device 2B illustrated in FIG. 11, first heater block 141 and second heater block 142 may have a shape corresponding to a half of a square divided by a diagonal line, or may have a shape corresponding to one piece of a square equally divided by a plurality of lines passing through discharging portion 130 as the center, such as a sixth or eighth part of the square. In this case, the reaction solution flowing through flow path 100 can be reacted in the reaction time closer to a predetermined reaction time as in microfluidic device 2 according to Embodiment 2.

Microfluidic devices 2A and 2B illustrated in FIGS. 10 and 11 each include flow path 100 disposed in the form of an approximately square spiral in a plan view, but the flow path may be disposed in any other form.

Figure 12:
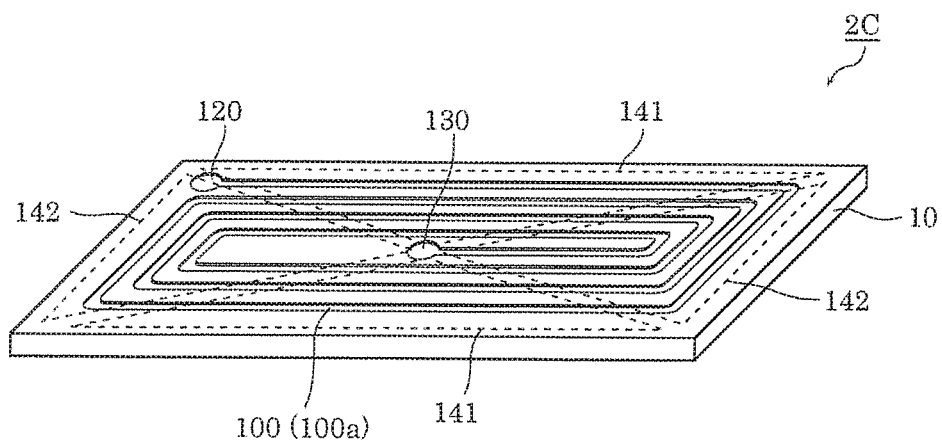
FIG. 12 is a perspective view illustrating a schematic configuration of a microfluidic device according to Modification 3 of Embodiment 2.

For example, as in microfluidic device 2C illustrated in FIG. 12, flow path 100 may be disposed in the form of an approximately rectangular spiral in a plan view. In this case, the reaction solution flowing through flow path 100 can be reacted in the reaction time closer to a predetermined reaction time as in microfluidic device 2 according to Embodiment 2.

Furthermore, in microfluidic device 2C illustrated in FIG. 12, flow path 100 corresponding to the long sides of the approximately rectangular spiral passes through the first temperature region (region corresponding to first heater block 141), which is a low temperature region, and flow path 100 corresponding to the short sides of the approximately rectangular spiral passes through the second temperature region (region corresponding to second heater block 142), which is a high temperature region.

In this case, the reaction solution flowing through flow path 100 can be reacted in the reaction time closer to a predetermined reaction time as in microfluidic device 2 according to Embodiment 2.

Moreover, in flow path 100 disposed in the form of an approximately square spiral, flow path 100 can be arranged efficiently as in FIGS. 10 and 11. The reaction of the reaction solution in the low temperature region needs a longer time than that in the high temperature region. Accordingly, as illustrated in FIG. 12, the long side portions of flow path 100 are disposed corresponding to the low temperature region, achieving a more efficient arrangement of the flow path.

Modification

The microfluidic device according to the present disclosure has been described based on Embodiments 1 and 2, but the present disclosure will not be limited to Embodiments 1 and 2.

For example, the microfluidic devices according to Embodiments 1 and 2 each include a serpentine flow path as flow path 100 (main flow path 100a) in reaction portion 110, enabling a flow PCR in which the temperature of the reaction solution containing the target nucleic acid is repeatedly changed, but the microfluidic device according to the present disclosure can use any other PCR method. In other words, any PCR method which can repeatedly change the temperature of the reaction solution containing a target nucleic acid may be used, rather than the flow PCR method. It should be noted, however, that the polymerase chain reaction can be performed more efficiently by the flow PCR method as used in the embodiments.

While heaters 140 are configured to provide the temperature regions having two different setting temperatures in Embodiments 1 and 2, three or more temperature regions having different setting temperatures may be disposed. In this case, the flow path is configured such that the reaction solution cyclically passes through these temperature regions having different temperatures.

While the temperatures of a plurality of temperature regions are set using the heater blocks in Embodiments 1 and 2, the temperatures may be set using another temperature control unit such as a Peltier device.

While the reaction solution is fed by capillary force in Embodiments 1 and 2, the reaction solution may be fed by any other method. For example, the reaction solution may be fed with a feeding pump, such as a syringe pump, connected to the flow path, or may be fed by a self-propelled method other than the capillary force. The feeding of the reaction solution using a feeding pump such as a syringe pump gradually reduces the solution feeding rate as the solution feeding distance is longer, although the degree of a reduction in solution feeding rate is not as much as in the feeding of the reaction solution by capillary force.

While flow path 100 according to Embodiment 2 is disposed in the form of an approximately circular or square spiral, the flow path may be disposed in any other form. For example, flow path 100 may be disposed in the form of any other polygonal (e.g., triangular or hexagonal) spiral or in the form of an arbitrarily curbed spiral.

While flow path 100 according to Embodiment 2 is a clockwise spiral, the flow path may be a counterclockwise spiral.

Besides, a variety of modifications of the embodiments conceived by those skilled in the art, and embodiments of any combination of the components and the functions in the embodiments without departing the gist of the present disclosure are also included within the present disclosure.

The invention claimed is:

1. A microfluidic device, comprising:
   a substrate;
   a flow path formed in the substrate through which a reaction solution flows;
   an introducing portion for introducing the reaction solution into the flow path;
   a discharging portion for discharging the reaction solution;
   a first heater block which generates a first temperature region, the first heater block disposed on the substrate; and
   a second heater block which generates a second temperature region, the second heater block disposed on the substrate, and both the first heater block and the second heater block are disposed on a same surface of the substrate,
   wherein the flow path passes alternately and repeatedly through the first temperature region and the second temperature region, the first temperature region and the second temperature region having different temperatures,
   the flow path includes repeating unit portions, each of the repeating unit portions passing through both the first temperature region and the second temperature region, the repeating unit portions having decreasing lengths from the introducing portion toward the discharging portion along the flow path,
   the flow path is a serpentine flow path including a plurality of linear portions, and a plurality of turns connecting the plurality of linear portions,
   the repeating unit portions passing through each of the first temperature region and the second temperature region are the plurality of linear portions,
   capillary force causes the reaction solution to flow from the introducing portion to the discharging portion,
   portions of the repeating unit portions, which pass through the first temperature region, have decreasing lengths from the introducing portion toward the discharging portion along the flow path, and
   portions of the repeating unit portions, which pass through the second temperature region, have decreasing lengths from the introducing portion toward the discharging portion along the flow path.

2. The microfluidic device according to claim 1,
   wherein the reaction solution contains a target nucleic acid, and
   the target nucleic acid is amplified by a polymerase chain reaction through passing of the reaction solution through the flow path.

3. The microfluidic device according to claim 1, wherein the introducing portion and the discharging portion are disposed on a same side of the substrate.

4. The microfluidic device according to claim 1, wherein the first heater block and the second heater block are disposed directly on the substrate.

* * * * *